United States Patent [19]

Bonnet

[11] Patent Number: 4,630,598
[45] Date of Patent: Dec. 23, 1986

[54] URETERO-RENOSCOPE

[75] Inventor: Ludwig Bonnet, Knittlingen, Fed. Rep. of Germany

[73] Assignee: Richard Wolf GmbH, Fed. Rep. of Germany

[21] Appl. No.: 734,678

[22] Filed: May 16, 1985

[30] Foreign Application Priority Data

May 29, 1984 [DE] Fed. Rep. of Germany ... 8416392[U]

[51] Int. Cl.⁴ .............................................. A61B 1/30
[52] U.S. Cl. ....................................................... 128/7
[58] Field of Search ................................. 128/4, 5, 6, 7

[56] References Cited

U.S. PATENT DOCUMENTS

| 939,034 | 11/1909 | Kolb | 128/6 |
| 2,112,056 | 3/1938 | Wappler | 128/7 |
| 2,129,391 | 9/1938 | Wappler | 128/6 |
| 4,557,255 | 12/1985 | Goodman | 128/7 |

FOREIGN PATENT DOCUMENTS 8322900 12/1983 Fed. Rep. of Germany .......... 128/7

Primary Examiner—William H. Grieb
Attorney, Agent, or Firm—Hill, Van Santen, Steadman & Simpson

[57] ABSTRACT

The ureteral renoscope comprises a shaft of oval or egg-shaped cross-section which is divided by an inner shaft into two axial passages of which one is traversed by an optical system and the other is traversed by an auxiliary instrument. Cross-sectional space is left free in each of said passages for the inflow and outflow of scavenging fluid.

9 Claims, 3 Drawing Figures

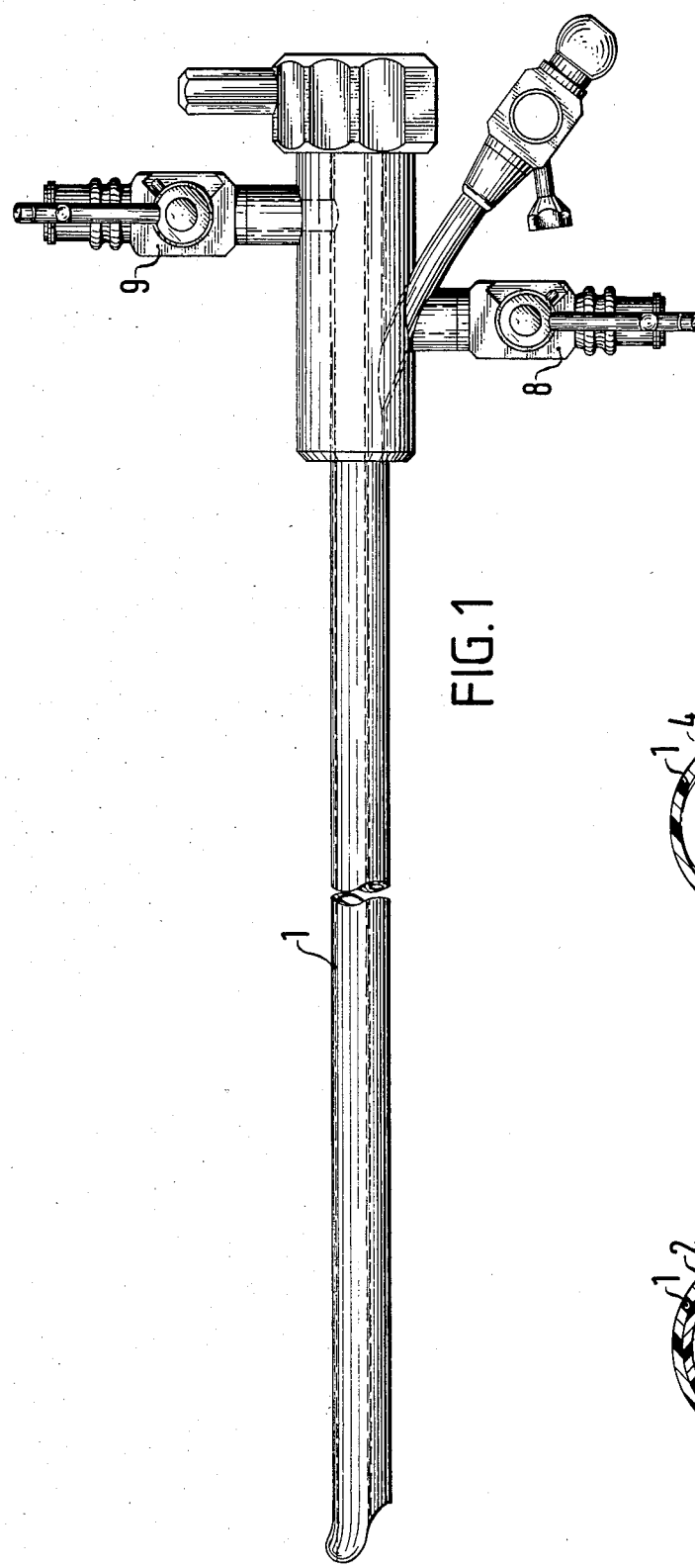
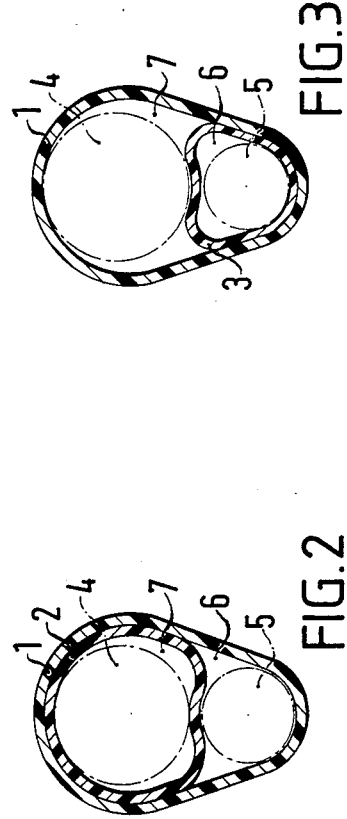
FIG.1
FIG.2
FIG.3

URETERO-RENOSCOPE

BACKGROUND OF THE INVENTION

1. Field of the Invention

The invention relates to a uretero-renoscope for removal of stones in the ureter under simultaneous visual observation with an optical system as well as having one or more auxiliary instruments located within the shaft of the ureteral renoscope.

2. Description of the Prior Art

According to the prior art, use is made of ureterorenoscopes which have no more than one passage for supplying and draining of the scavenging fluid, so that constant alternation between inflow and outflow is required. In view of the intermittent operation, the case may arise during the disintegration of a stone present in the ureter, that small or very small concretions may be flushed into the pelvis of the kidney in an accidential and undesirable manner, which may again cause another stone to be formed. Furthermore, the scavenging fluid accumulated in the pelvis of the kidney may cause a functional breakdown of the kidney by damaging the kidney parenchyma.

SUMMARY OF THE INVENTION

The object of the invention consequently consists in providing a scavenging or flushing system in the case of uretero-renoscopes for removal of stones, which allows direct flushing-out of concretions occurring during disintegration of stones and prevents damage to the kidney parenchyma by accumulation of the scavenging fluid in the pelvis of the kidney.

In accordance with the invention, this problem is resolved in that the uretero-renoscope shaft, which is preferably of an oval cross-section, is divided into two sections by an inner shaft, and that the free spaces left within the respective sections after passing an optical system through the one section and an auxiliary instrument through the other form respective passages for the inflow and outflow of scavenging fluids.

Thanks to this solution, an effective constant flushing operation is secured for a uretero-renoscope, which prevents the build-up of a high pressure immediately in front of the stone within the ureter, and thereby prevents the displacement of the stone or the flushing of stone accretions into the pelvis of the kidney.

A particularly advantageous constant flushing action is secured when the inflow and outflow passages have the same cross-sectional area or when the outflow passage has a greater cross-section than the inflow passage, thereby preventing unfavourable pressure conditions in front of the stone or within the pelvis of the kidney

BRIEF DESCRIPTION OF THE DRAWINGS

FIG. 1 shows a sideview of a uretero-renoscope,

FIGS. 2 and 3 show two alternative cross-sectional views for the renoscope shaft according to FIG. 1.

DETAILED DESCRIPTION OF THE PREFERRED EMBODIMENTS

The uretero-renoscope according to the invention comprises a cross-sectionally elliptical or oval main hollow shaft 1 whose cross-section is divided by an inner hollow shaft 2 (FIG. 2) or 3 (FIG. 3). According to FIG. 2 the inner hollow shaft or tube 2 is received within the upper cross-sectional section of the renoscope shaft 1 and has an optical system 4 passed through it whereas an auxiliary instrument 5 is passed through the remaining lower cross-sectional section of the hollow shaft 1.

Two passages 6 and 7 are formed according to FIG. 2 between the optical system 4 and the inner surface of the hollow shaft 2 as well as between the auxiliary instrument 5 and the inner surface of the outer shaft 1 in view of the division of the shaft by means of the inner shaft 2 or 3 and appropriate construction of the wall of the inner shaft. One passage 6 is connected via a connector 8 to the supply of a flushing fluid, and the other passage 7 is connected to a connector 9 for the outflow of the flushing fluid. To this end, the passages 6 and 7 are advantageously of identical cross-sectional area, or the outflow passage 7 has a slightly larger cross-section, to prevent accumulations during constant flushing. The connectors 8 and 9 each have on-off valves and are provided on a proximal end portion of the renoscope which is also provided with conventional coaxial connecting means for the optical system 4 and a connector branching out at an angle to the main shaft for the auxiliary instrument 5.

By contrast to FIG. 2, the procedure applied according to FIG. 3 is that the inner hollow shaft 3 receives the auxiliary instrument 5 and the outer shaft 1 receives the optical system 4, and that the remaining free passage cross-sections are constructed to either have the same cross-sectional area or to have the passage 7 with a greater cross-section than the passage 6.

What is claimed is:

1. In an uretero-renoscope comprising a hollow main shaft with axial passage means therethrough for receiving both an optical system with an outer surface and an auxiliary instrument with an outer surface and for the passage of a scavenging fluid, an improvement comprising said axial passage means being formed by a single inner shaft being received within said hollow main shaft, said inner shaft having an axial passage therethrough and having a smaller cross-sectional area than the inner cross-section of said hollow main shaft to divide said inner cross-section into two separate passages with inner surfaces to separately accommodate said optical system and said auxiliary instrument respectively, each of said two separate passages with the respective optical system and auxiliary instrument in position a providing free space between the inner surface of each passage and an outer surface for the passing of scavenging fluid so that the inflow and outflow of said scavenging fluid can proceed simultaneously.

2. In an uretero-renoscope according to claim 1, wherein said main shaft is of an egg-shaped cross-section.

3. In an uretero-renoscope according to claim 1, wherein the said free space has the same cross-sectional area in each of said two separate passages.

4. In an uretero-renoscope according to claim 1, wherein the free space for the outflow of scavenging fluid has a greater cross-sectional area than that of the free space for the inflow of said fluid.

5. An uretero-renoscope consisting of;
   a hollow main shaft;
   a single hollow inner shaft dividing the cross-section of said main shaft into two axial passages with inner surfaces;
   an optical system with an outer surface passing through one of said two axial passages and an auxiliary instrument with an outer surface passing through the other of said two axial passages, wherein in each passage free cross-sectional space is provided between said inner surface and outer surface for the passage of scavenging fluid through each of said axial passages alongside said optical system and said auxiliary instrument, means being provided for supplying said fluid to one of said axial passages and for draining said fluid from the other of said passages.

6. An uretero-renoscope according to claim 5, wherein said main shaft has an egg-shaped cross-section with a widened portion and a narrower portion.

7. An uretero-renoscope according to claim 6, wherein said optical system passes through said widened portion of the main shaft and said auxiliary instrument passes through said narrower portion.

8. An uretero-renoscope according to claim 5, wherein said optical system passes through the axial passage defined within said hollow inner shaft.

9. An uretero-renoscope according to claim 5, wherein said auxiliary instrument passes through the axial passage defined within said hollow inner shaft.

* * * * *